US007652196B2

(12) United States Patent
Ammerlaan

(10) Patent No.: US 7,652,196 B2
(45) Date of Patent: Jan. 26, 2010

(54) COS FOR MECHANICAL HARVEST

(75) Inventor: Aad Ammerlaan, Aramon (FR)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 24 days.

(21) Appl. No.: 11/528,849

(22) Filed: Sep. 28, 2006

(65) Prior Publication Data

US 2008/0083044 A1 Apr. 3, 2008

(51) Int. Cl.
*A01H 1/00* (2006.01)
*A01H 4/00* (2006.01)
*A01H 5/00* (2006.01)
*A01H 5/10* (2006.01)

(52) U.S. Cl. ....................... 800/305; 435/410; 800/260; 800/298

(58) Field of Classification Search ....................... None
See application file for complete search history.

(56) References Cited

U.S. PATENT DOCUMENTS

| | | | | |
|---|---|---|---|---|
| 6,649,815 | B1 * | 11/2003 | Avila et al. | 800/305 |
| 6,689,941 | B2 * | 2/2004 | Waycott | 800/305 |
| 6,841,723 | B2 * | 1/2005 | Avila et al. | 800/305 |

* cited by examiner

*Primary Examiner*—David H Kruse
(74) *Attorney, Agent, or Firm*—Frommer Lawrence & Haug LLP; Thomas J. Kowalski

(57) ABSTRACT

The present invention relates to a *Lactuca sativa* L. var. longifolia Lam seed which has a solid main vein and narrow base leaves, dark green outer leaves, short core, absence of fringe burn, and absence of tipburn. A specific embodiment is designated 41-69 RZ, referred to as Actarus. The present invention also relates to a *Lactuca sativa* L. var. longifolia Lam plant produced by growing the "41-69 RZ" ("Actarus") seed. The invention further relates to methods for producing the lettuce cultivar, represented by lettuce variety 41-69 RZ.

17 Claims, 1 Drawing Sheet

COS FOR MECHANICAL HARVEST

BACKGROUND OF THE INVENTION

1. Field of the Invention

The present invention relates to a new lettuce (*Lactuca sativa*) variety which is suitable for mechanical harvest.

2. Description of Related Art

Romaine lettuce should provide a product at harvestable stage, which is accepted by processing industry and/or consumers. Therefore, the harvestable product should not have tipburn, should have a short core, and it should have a dark green outer leaf colour. Further it should be sufficiently headed, and as a result of this heading provide sufficient yellow-coloured heart leaves.

Until now mature romaine lettuce is mainly harvested by hand. This harvesting process is labour-intensive, and relatively labourer-unfriendly. As it is getting more and more costly to hire labourers that want to work outdoor in the field, close to the ground and under all kinds of adverse weather conditions, there is strong interest of the lettuce industry to mechanize this manual harvesting process. However, until now the lack of uniform quality among mature plants is a big problem for mechanised harvest. Poor quality of basal leaves, internal breakdown of heart leaves due to tipburn, fringe burn of leaf margins, and fast bolting are the main quality problems. If one would like to mechanise the harvest process, these quality problems would result in additional hand sorting, which is costly, and/or a very low net yield, if the plant parts with a high risk of quality problems are mechanically discarded.

The latter approach is chosen by some producers that produce romaine hearts, i.e. the intact yellow-green heart of the romaine lettuce without the green outer leaves. For producers that produce romaine lettuce for processing, i.e. pre-washed and pre-cut leaves, this is not feasible because of three major constraints. The first is the requirement for a mix of green and yellow leaves, which requires the preservation of the green outer leaves. The second constraint is the strongly reduced net yield, which is a result of the fact that an automated knife should cut through the leaf but not through the core. Especially fast bolting lettuce varieties are unacceptable for mechanised harvest of romaine lettuce for processing purposes because of their long core. The third constraint is caused by the use of mechanically-driven horizontal knives that easily damage the hollow main veins of romaine leaves and cut halfway through the prostrate, round-shaped, lower outer leaves, which results in wide cut surfaces. Cutting damage on a leaf with a hollow main vein is often not restricted to the cut surface but bruising extends into the leaf along the main vein.

It is the object of the invention to provide a new type of romaine or cos lettuce, which is suitable for mechanical harvest with a simple horizontal knife. The harvested product is meant for processing purposes.

SUMMARY OF THE INVENTION

The present invention fulfils this need by providing a new romaine, or cos lettuce (*Lactuca sativa* L. var. longifolia Lam) plant, which exhibits a combination of leaves with a solid main vein and narrow base leaves.

In particular, the present invention provides the *Lactuca sativa* L. var. longifolia Lam plant with the following additional characteristic: dark green outer leaves.

In particular, the present invention provides the *Lactuca sativa* L. var. longifolia Lam plant with one or more of the following additional characteristics: short core, absence of fringe burn, and absence of tipburn.

More in particular, the present invention provides seeds of the *Lactuca sativa* L. var. longifolia Lam plant designated as 41-69 RZ, referred to as Actarus.

The present invention also provides a lettuce plant or parts thereof produced by growing the seed of lettuce cultivar 41-69 RZ.

The present invention further provides pollen, ovules, and tissue cultures of regenerable cells from the plant produced by growing the seed of lettuce cultivar 41-69 RZ, in which the cells or protoplasts of the tissue that are cultured are produced from a tissue selected from leaves, pollen, embryos, cotyledon, hypocotyls, meristematic cells, roots, root tips, anthers, flowers, seeds or stems.

The present invention still further provides a lettuce plant regenerated from the above-described tissue cultures, in which the regenerated plant has all of the morphological and physiological characteristics of lettuce cultivar 41-69 RZ.

The present invention also provides a transgene of the seed of lettuce cultivar 41-69 RZ.

The present invention further provides a method for producing a hybrid lettuce seed comprising crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-69 RZ.

The present invention still further provides a method for developing a lettuce cultivar having leaves with a solid main vein and narrow base leaves comprising crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having leaves with a solid main vein and narrow base leaves.

DETAILED DESCRIPTION OF THE INVENTION

Figure 1:
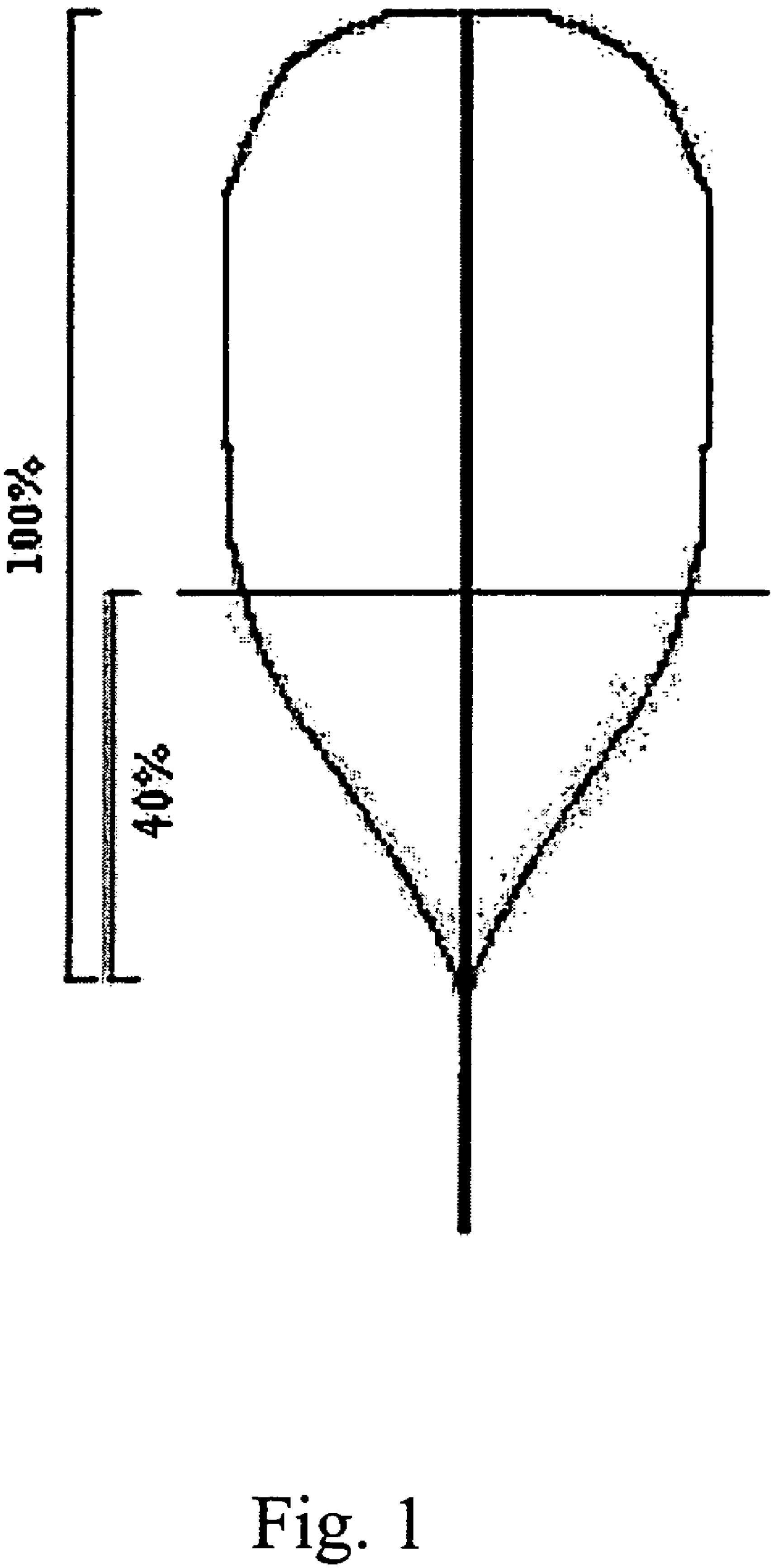
FIG. 1 shows a transverse section at 40% of leaf lamina length to observe solidness of main vein.

The present invention provides a *Lactuca sativa* L. var. longifolia Lam (romaine or cos lettuce) plant comprising leaves with a solid main vein and narrow base leaves.

In particular, the present invention provides the *Lactuca sativa* L. var. longifolia Lam plant with the following additional characteristic: dark green outer leaves.

In particular, the present invention provides the *Lactuca sativa* L. var. longifolia Lam plant with one or more of the following additional characteristics: short core, absence of fringe burn, and absence of tipburn.

In particular, the present invention provides seeds of the *Lactuca sativa* L. var. longifolia Lam plant designated as 41-69 RZ, referred to as Actarus.

Seeds of lettuce cultivar 41-69 RZ have been deposited on Sep. 20, 2006 under the terms of the Budapest treaty with the National Collections of Industrial, Marine and Food Bacteria (NCIMB) in Bucksburn, Aberdeen AB21 9YA, Scotland, UK and have been assigned NCIMB Accession No. 41440. Deposited seed will be irrevocably and without restriction or condition released to the public during the term of any patent issued from this application.

As used herein, romaine is *Lactuca sativa* L. var. longifolia Lam, also known as cos. The plant develops in an upright open or upright compact growing habit with coarse textured leafs. The younger leaves are longer than they are wide, fifteen cupping together to form an elongated loose head. Leaf margins are often entire or undulated, rarely frilled. Outer leaves range in color from light green to dark green. Inner heart leaves are smaller and range from light yellow to light green in color.

As used herein, a solid main vein is the main vein of a fully grown tenth to fifteenth leaf, which is characterised by the fact that the vein is not hollow, which is observed by visual inspection of a transverse section of the leaf. The transverse section should be made at 40% of the total leaf length, starting from the leaf base (see FIG. 1). For comparison two standard varieties can be used: Maximus, with hollow veins, and Tiberius, with solid veins.

As used herein, a narrow base leaf is characterised by a length/width-ratio of 1.5 or higher. A mature romaine lettuce plant has got narrow base leaves if the average length/width-ratio of the fully grown tenth to the fifteenth leaf is 1.5 or higher. For comparison two standard varieties can be used: Maximus with broad base leaves, and Chilim with narrow base leaves.

As used herein, dark green outer leaves are defined by the colour of a fully grown tenth to fifteenth leaf, which should be similar to or darker than 137B, 138A, 144A, or 146A on the RHS colour chart (The Royal Horticultural Society, London, UK).

As used herein, a short core is defined by measuring the length of the core of a harvested mature plant with outer leaves attached. The plant should be grown outdoor under long-day conditions: sowing 5-15 days before the longest day in a mild mid-latitude climate with a warm summer (Köppen-classification: Csb or Cfb; McKnight & Hess, 2000. Physical Geography: A Landscape Appreciation. Upper Saddle River, N.J.: Prentice Hall). A mature plant grown under these conditions is defined as being headed and having a weight of 800-1200 g after harvest. The core of such a plant is defined as ‘short’ if its length is less than or equal to 8 cm.

As used herein, absence of fringe burn is established by growing plants in outdoor conditions in a winter production area for lettuce with an average daily temperature of the coldest month between 11 and 14° C., for example Cartagena, Spain or Yuma, USA. The growing cycle under these conditions should be at least 16 weeks from sowing a seed to harvesting a mature plant. Harvesting the mature plant should take place in the month after the coldest month. Absence of fringe burn is defined by observing the leaf margin of the tenth until the fifteenth leaf. Absence of fringe burn is established, if for each of these leaves less than 2% of the perimeter of the leaf margin is necrotic.

As used herein, absence of tipburn is established by growing plants in outdoor conditions in spring conditions in a winter production area for lettuce with an average daily temperature of the coldest month between 11 and 14° C., for example Cartagena, Spain or Yuma, USA. Harvesting the mature plant should take place in the third month after the coldest month. Absence of tipburn is defined by observing the ten most recently developed heart leaves longer than 5 cm. Absence of tipburn is established, if for each of these leaves less than 1% of the perimeter of the leaf margin is necrotic. The additional requirement for establishing absence of tipburn is that the comparison variety Maximus, grown under the same conditions with the same sowing and harvest date, shows presence of tipburn, and a second comparison variety Optimus, grown under the same conditions with the same sowing and harvest date, shows absence of tipburn. Presence of tipburn is established, if for at least one out of the ten most recently developed heart leaves longer than 5 cm, at least than 1% of the perimeter of the leaf margin is necrotic.

In an embodiment of the present invention, there is provided a lettuce plant or parts thereof produced by growing the seed of lettuce cultivar 41-69 RZ.

In another embodiment, there is provided pollen, ovules, and tissue cultures of regenerable cells from the plant produced by growing the seed of lettuce cultivar 41-69 RZ, in which the cells or protoplasts of the tissue that are cultured are produced from a tissue selected from leaves, pollen, embryos, cotyledon, hypocotyls, meristematic cells, roots, root tips, anthers, flowers, seeds or stems.

In still another embodiment, there is provided a transgene of the seed of lettuce cultivar 41-69 RZ.

In a further embodiment, there is provided a lettuce plant regenerated from the above-described tissue cultures, in which the regenerated plant has all of the morphological and physiological characteristics of lettuce cultivar 41-69 RZ.

In still a further embodiment, a method is provided for producing a hybrid lettuce seed comprising crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-69 RZ.

In still another embodiment, a method is provided for developing a lettuce cultivar having leaves with a solid main vein and narrow base leaves comprising crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having leaves with a solid main vein and narrow base leaves.

In a preferred embodiment, the specific type of breeding method employed for developing a lettuce cultivar is pedigree selection, where both single plant selection and mass selection practices are employed. Pedigree selection, also known as the “Vilmorin system of selection,” is described in Fehr, W., Principles of Cultivar Development, Volume I, MacMillan Publishing Co., which is hereby incorporated by reference.

When pedigree selection is applied, in general selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce F1 offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The F1 may be self-pollinated to produce a segregating F2 generation. Individual plants may then be selected which represent the desired phenotype in each generation (F3, F4, F5, etc.) until the traits are homozygous or fixed within a breeding population.

The present invention is more particularly described in the following non-limiting example, which is intended to be illustrative only, as numerous modifications and variations therein will be apparent to those skilled in the art.

EXAMPLE 1

Development and Characteristics of Lettuce Cultivar 41-69 RZ

The breeding history of Actarus started in Aramon, France in 1995 with a cross between a plant from the grasse lettuce cultivar 'Bambi' (Rijk Zwaan) as mother and a plant from the Bremia-resistant indoor batavia breeding line '95A.30955' (Rijk Zwaan) as father with the aim to introduce resistance against *Bremia lactucae* (Bl-resistance) in the grasse type.

An F3-plant, '97A.23750', derived from this cross was selected in July 1997 in Aramon, France and used as a father in a cross with a mother plant of the romaine cultivar 'Fransesca' (S&G) to introduce Bl-resistance in the romaine type. An F3-plant, '99A.23056' derived from this cross was selected in April 1999 in Aramon, France for its leaves with a solid main vein, its short core, dark green colour, absence of fringe burn and its Bl-resistance and used as a father in a cross with a mother plant of the romaine cultivar 'Chilim' (S&G). 'Chilim' was chosen for its narrow base leaves.

A resulting F1-plant was grown in Aramon, France to produce F2-seed designated 00A.47131. This F2-seed was sown in a late summer trial in Aramon, France in 2000. In October 2000 an F2-plant was selected for being a romaine type with leaves with a solid main vein, a short core and narrow base leaves. The F2-plant produced F3-seed, designated 01A.48557, which was sown in a summer trial in Aramon, France in 2001. In July 2001 an F3-plant was selected from the trial for being a dark green romaine type with leaves with a solid main vein, absence of tipburn, a short core, and narrow base leaves. The F3-plant produced F4-seed, designated 02A.50500, which was sown in a winter trial in a plastic tunnel in Aramon, France in 2001. In February 2002 an F4-plant was selected from the trial for being a dark green romaine type with leaves with a solid main vein, absence of fringe burn and narrow base leaves. The F4-plant produced F5-seed, designated 02A.51813, which was sown in a spring trial in Aramon, France in 2003. In April 2003 an F5-plant was selected from the trial for being a dark green romaine type and with leaves with a solid main vein, absence of tipburn, and narrow base leaves. The F5-plant produced F6-seed, designated 03A.50148, which was sown in a late summer trial in Aramon, France in 2003. In October 2003 an F6-plant was selected from the trial for being a dark green romaine type and with leaves with a solid main vein, a short core, absence of tipburn, and narrow base leaves. The F6-plant produced F7-seed, designated 04A.51992, which was sown in an early summer trial in Fijnaart, the Netherlands in 2004. In June 2004 an F7-plant was selected from the trial for being a dark green romaine type and with leaves with a solid main vein, a short core, absence of tipburn, and narrow base leaves. The F7-plant produced F8-seed, designated 05A.50606, which was uniform for type, field performance, bolting, absence of tipburn and fringe burn, leaves with a solid main vein and narrow base leaves (all based on several trials in 2005).

The F8-seed was used to sow a multiplication in Daylesford, Australia in October, 2004. The plants showed phenotypical uniformity during seed production and seed was harvested for further trialling in 2005 on confidential sites. The seed lot was designated by the introduction number '41-69 RZ' and referred to as 'Actarus'.

The distinct resistance characteristics of 'Actarus' offer a significant advantage for growers trying to grow romaine lettuce at a low cost price. The variety can be mechanically harvested with standard equipment for mechanical harvesting of babyleaf lettuce and/or spinach. The resulting reduction in harvesting labour is not significantly affected by the labour required for sorting the harvested product, because pieces of the main core, and leaves with fringe burn or tipburn are virtually absent. Also cutting damage on the main vein of the leaves is minimal, because of the solidness of the vein. The harvested leaves are very uniform due to the fact that also the older base leaves show a small cut surface and are longer than they are wide, just like the younger leaves. The dark green colour of the outer leaves provides an attractive contrast to the more yellow colour of the inner heart leaves.

In the Table that follows, the traits and characteristics of the *Lactuca sativa* L. var. longifolia Lam romaine lettuce plant referred to as "Actarus" and having the designation 41-69 RZ, are given compared to the comparison varieties mentioned, referred to as "Tiberius", "Maximus", "Optimus", and "Chilim".

| Character Type | "Actarus" romaine or cos | "Tiberius" romaine or cos | "Maximus" romaine or cos | "Optimus" romaine or cos | "Chilim" romaine or cos |
|---|---|---|---|---|---|
| hollow/solid main vein | solid | solid | hollow | hollow | hollow |
| broad/narrow base leaves | narrow | broad | broad | broad | narrow |
| blond/dark green colour | dark | dark | dark | blond | blond |
| core length | short | long | short | short | long |
| tipburn | absent | present | present | absent | present |
| fringe burn | absent | absent | absent | present | present |

While the invention has been particularly shown and described with reference to preferred embodiments thereof, it will be understood by those skilled in the art that various alterations in form and detail may be made therein without departing from the spirit and scope of the invention.

The invention claimed is:

1. A lettuce plant designated 41-69 RZ, referred to as Actarus, representative seed of which having been deposited under NCIMB Accession No. 41440, wherein said plant has leaves with a solid main vein and narrow base leaves, dark green outer leaves, short core, absence of fringe burn, and absence of tipburn.

2. A seed of the plant of claim 1.

3. A parts of the plant of claim 1 that is suitable for sexual reproduction.

4. A part as claimed in claim 3, selected from the group consisting of microspores, pollen, ovaries, ovules, embryo sacs, egg cells.

5. A part of the plant of claim 1 that is suitable for vegetative reproduction.

6. A part as, claimed in claim 5 selected from cuttings, roots, stems, cells, protoplasts.

7. A tissue culture of a lettuce plant of claim 1.

8. A tissue culture as claimed in claim 7, which is derived from leaves, pollen, embryos, cotyledon, hypocotyls, meristematic cells, roots, root tips, anthers, flowers, seeds and stems.

9. A plant grown from the seed as claimed in claim 2 having leaves with a solid main vein and narrow base leaves, dark green outer leaves, short core, absence of fringe burn, and absence of tipburn.

10. A plant regenerated from the part as claimed in claim 3 having leaves with a solid main vein and narrow base leaves, dark green outer leaves, short core, absence of fringe burn, and absence of tipburn.

11. A plant regenerated from the tissue culture as claimed in claim 7 having leaves with a solid main vein and narrow base leaves, dark green outer leaves, short core, absence of fringe burn, and absence of tipburn.

12. A progeny of a lettuce plant of claim 1 having leaves with a solid main vein and narrow base leaves, dark green outer leaves, short core, absence of fringe burn, and absence of tipburn.

13. The progeny as claimed in claim 12 produced by sexual or vegetative reproduction of said lettuce plant or a progeny plant thereof having leaves with a solid main vein and narrow base leaves, dark green outer leaves, short core, absence of fringe burn, and absence of tipburn.

14. A progeny of a lettuce plant of claim 9 having leaves with a solid main vein and narrow base leaves, dark green outer leaves, short core, absence of fringe burn, and absence of tipburn.

15. A progeny of a lettuce plant of claim 10 having leaves with a solid main vein and narrow base leaves, dark green outer leaves, short core, absence of fringe burn, and absence of tipburn.

16. A progeny of a lettuce plant of claim 11 having leaves with a solid main vein and narrow base leaves, dark green outer leaves, short core, absence of fringe burn, and absence of tipburn.

17. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

* * * * *

UNITED STATES PATENT AND TRADEMARK OFFICE

CERTIFICATE OF CORRECTION

PATENT NO. : 7,652,196 B2
APPLICATION NO. : 11/528849
DATED : January 26, 2010
INVENTOR(S) : Aad Ammerlaan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this

Twenty-third Day of November, 2010

David J. Kappos

*Director of the United States Patent and Trademark Office*

UNITED STATES PATENT AND TRADEMARK OFFICE

CERTIFICATE OF CORRECTION

PATENT NO. : 7,652,196 B2
APPLICATION NO. : 11/528849
DATED : January 26, 2010
INVENTOR(S) : Adrianus Martinus Jozeph Ammerlaan It is certified that error appears in the above-identified patent and that said Letters Patent is hereby corrected as shown below:

On the title page
Item (75) Inventor: Change “Aad Ammerlaan” to --Adrianus Martinus Jozeph Ammerlaan--

Signed and Sealed this
Fourteenth Day of June, 2016

Michelle K. Lee
*Director of the United States Patent and Trademark Office*